(12) United States Patent
Bahrmann et al.

(10) Patent No.: US 6,703,507 B2
(45) Date of Patent: Mar. 9, 2004

(54) IONIC LIQUIDS AND PRODUCTION AND USE THEREOF

(75) Inventors: Helmut Bahrmann, Hamminkeln (DE); Hans Bohnen, Moers (DE)

(73) Assignee: Celanese Chemicals Europe GmbH (DE)

( * ) Notice: Subject to any disclaimer, the term of this patent is extended or adjusted under 35 U.S.C. 154(b) by 70 days.

(21) Appl. No.: 09/959,059

(22) PCT Filed: Apr. 18, 2000

(86) PCT No.: PCT/EP00/03499

§ 371 (c)(1), (2), (4) Date: Oct. 16, 2001

(87) PCT Pub. No.: WO00/66597

PCT Pub. Date: Nov. 9, 2000

(65) Prior Publication Data

US 2002/0161261 A1 Oct. 31, 2002

(30) Foreign Application Priority Data

Apr. 29, 1999 (DE) .......................... 199 19 494

(51) Int. Cl.[7] .............................. C07F 9/58; C07F 9/141
(52) U.S. Cl. .......................................... 546/24; 568/374
(58) Field of Search ............................. 568/374; 546/24

(56) References Cited

U.S. PATENT DOCUMENTS 5,892,124 A    4/1999   Olivier et al. .............. 568/374

FOREIGN PATENT DOCUMENTS

| EP | 0003554 | 8/1979 |
| FR | 0776880 | 6/1997 |
| GB | 2337754 | 12/1999 |

OTHER PUBLICATIONS

Bohm et al, Nonaqueous . . . of Chloroarenes. No. 6, Vol 6 pp. 1017–1025.

Analytica Chimica Acta, Pardue et al, vol. 218 (1989) (24 Pages).

*Primary Examiner*—Joseph K. McKane
*Assistant Examiner*—Kamal Saeed
(74) *Attorney, Agent, or Firm*—Muserlian, Lucas and Mercanti

(57) ABSTRACT

The invention relates to novel ionic liquids and to the production and use thereof. The novel ionic liquids are salts of sulphonated or carboxylated triesters of phosphorous acid as the anionic component and ammonium ions, which can be substituted with organic radicals, as the cationic component.

19 Claims, No Drawings

IONIC LIQUIDS AND PRODUCTION AND USE THEREOF

This application is a 371 of PCT/EP00/03499 filed Apr. 18, 2000.

The present invention relates to novel ionic liquids which are used as media for carrying out chemical reactions, particularly reactions which proceed in the presence of catalysts. The novel ionic liquids are salts of sulfonated or carboxylated triesters of phosphorous acid as anionic constituent and ammonium ions, which may be substituted by organic radicals, as cationic constituent.

Ionic systems which melt at low temperature and are liquid in a range from about room temperature to a few hundred degrees Celsius can be used as reaction media for a wide range of chemical processes. When used in this way, the ionic liquids frequently fulfil a double task: they serve not only as solvent for the reactants but at the same time as catalysts or catalyst components for the reaction of the reactants to form the desired product. The advantages of such a reaction in a homogeneous phase are known. High reaction rates are frequently achieved and the chemoselectivity, regioselectivity, stereoselectivity and entantioselectivity of the reaction can often be controlled simply and precisely. In some cases, the reaction product is not soluble in the reaction medium. In such a case, the ease of separating product, catalyst and starting material is a further advantage.

In another variant of the chemical reaction procedure, use is made of ionic liquids which serve only as solvent for the catalyst and are immiscible with the reactants and the reaction product. In this case, the reaction between the reactants occurs at the phase interface to the catalyst solution and the reaction product forms a phase separate from the catalyst. This process, which can be described as a reaction in two heterogeneous liquid phases, is advantageous whenever the reaction product has to be removed quickly from the reaction mixture so that it does not undergo further reactions. In addition, catalyst and reaction product can be separated from one another under mild conditions, in particular without thermal treatment methods which can lead to damage to the constituents of the reaction mixture. In the case of catalytic reactions which proceed in heterogeneous systems, too, the ionic liquid can not only act as solvent for the catalyst but can itself be a constituent of the catalyst.

Further advantages of ionic liquids are their chemical and thermal stability which make them suitable for a wide range of applications. Owing to their negligible vapor pressure, they emit no vapors and as a result do not contribute to air pollution and are, compared to conventional solvents used as reaction media, remarkably environmentally friendly. Owing to the many advantages indicated, ionic liquids are attracting increasing interest as reactive components or as reaction auxiliaries in numerous industrial syntheses.

According to CHEMTECH, September 1995, pages 26ff, ionic liquids which are liquid at room temperature, e.g. a mixture of 1,3-dialkylimidazolium chloride, preferably 1-n-butyl-3-methylimidazolium chloride ([BMI]$^+$[Cl]$^-$ for short), and aluminum chloride and/or ethylaluminum chloride, are used as nonaqueous solvents for catalysts. As an example of a reaction in which such catalyst solutions are used, the publication cites the dimerization of olefins in the presence of nickel complexes as catalyst, e.g. the dimerization of propene to form isomeric hexenes and the dimerization of butene to form isooctenes. The reaction mixture forms two phases, of which the reaction product forms the upper phase and the lower phase consists of the catalyst solution. After separation of the phases, the catalyst solution can be returned to the process.

Am.Chem.Soc., Div. Pet. Chem. (1992), 37, pages 370ff, discloses the dimerization of propene in the presence of a solution of $NiCl_2.(PR_3)_2$, ($R=i-C_3H_7$), in a mixture of [BMI]$^+$[Cl]$^-$ and $AlCl_3$ as ionic liquid.

The use of low-melting phosphonium salts, e.g. tetrabutylphosphonium bromide, as solvent in hydroformylation reactions is described in Journal of Molecular Catalysis, 47 (1988), pages 99ff. Here, the hydroformylation of 1-octene using ruthenium carbonyl complexes in the presence of nitrogen- and phosphorus-containing ligands, e.g. 2,2'-bipyridyl or 1,2-bis(diphenylphosphino)ethane, at from 120 to 180° C. gives a mixture of n-nonanol and n-nonanal containing up to 69% by weight of the alcohol, based on the reaction mixture. A costly distillation is therefore necessary to isolate the desired n-nonanal.

European patent application EP-A-0 776 880 teaches the hydroformylation of olefins in the presence of quaternary ammonium and/or phosphonium salts as solvents for the catalyst. Preference is given to salts containing [BMI]$^+$ as cation. Salts of quaternary diamines in which the cation has the formula

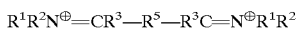

where $R^1$, $R^2$, $R^3$ are identical or different and are each hydrogen or a hydrocarbon radical having from 1 to 12 carbon atoms and $R^5$ is an alkylene radical, e.g. methylene, ethylene or propylene, or a phenylene radical, are used in this publication. Suitable anions are, for example, hexafluorophosphate, hexafluoroantimonate, tetrachloroaluminate or tetrafluoroborate. These quaternary ammonium and/or phosphonium salts are liquid below 90° C., preferably below 85° C. and particularly preferably below 50° C.

The hydroformylation catalyst dissolved in these salts comprises cobalt, rhodium, iridium, ruthenium, palladium or platinum as active metal and a tertiary phosphine or tertiary sulfonated phosphine, a tertiary arsine, tertiary stilbene or a phosphite as ligand. The molar ratio of ligand to metal is 9.5. The catalytically active metals are used as compounds, for example rhodium in the form of dicarbonylrhodium acetylacetonate or rhodium carbonyl $Rh_6(CO)_{16}$. The hydroformylation catalyst is formed from them under the reaction conditions. The hydroformylation reaction is particularly preferably carried out at from 30 to 90° C.

According to Angew. Chem. 1995, 107, No. 23/24, pages 2941 ff, too, hydroformylation reactions can be carried out using 1,3-dialkylimidazolium salts which are liquid at room temperature as catalyst-containing solvent which is immiscible with the organic reaction mixture. For this purpose, dicarbonylrhodium acetylacetonate is added as catalyst precursor to a solution of triphenylphosphine in [BMI]$^\oplus$[PF$_6$]$^\ominus$; the molar ratio of phosphorus(III) to rhodium can vary from 3 to 10. The catalyst is preformed by means of synthesis gas (volume ratio of hydrogen to carbon monoxide=1:1). 1-Pentene is subsequently reacted with synthesis gas of the same composition at a temperature of 80° C. In this case too, the organic product phase can be separated in a simple manner from the catalyst-containing, nonaqueous ionic liquid by decantation.

The ionic liquids used for dissolving the catalyst in known hydroformylation processes are salts whose anions display no ligand properties toward the catalytically active metal and are therefore not capable of forming complexes. In favorable cases, they are present as inerts in the reaction mixture and do not participate in the reaction. However, it is not impossible for them to have an adverse effect on the reaction, e.g. for them to reduce the reaction rate or decrease the selectivity.

Furthermore, the prior art (cf. Angew. Chem. 1995, 107, p. 2941 and EP-A-0 776 880) states that the molar ratio of ligand/metal, e.g. phosphorus/rhodium, varies in the range from 3 to 10. Higher molar ratios are obviously regarded as unsuitable, although increasing the proportion of ligand, based on the metal, should improve the stability of the catalytically active complex. It is possible that the solubility of the compounds acting as ligands in the hitherto customary ionic liquids is limited, so that they precipitate from the solution when a maximum concentration is exceeded and thus leave the catalyst phase.

EP-A2-0 353 770 describes carrying out catalytic processes in a homogeneous phase and in the presence of catalyst systems comprising complexes of transition metals of group VIII of the Periodic Table and ionic phosphites as ligands. The term "ionic phosphites" refers to salts of esters of phosphorous acid whose alcohol components are substituted by sulfonate or carboxylate groups and are therefore capable of salt formation. The ionic phosphites are usually present in excess, i.e. free ligands which have not formed a bond to the transition metal are present in addition to the metal complexes. The catalyst system, i.e. transition metal and ionic phosphite, is used as a solution in an organic solvent, e.g. aliphatic aldehydes having from 3 to 6 carbon atoms in the molecule; the phosphite itself does not act as solvent. To improve the solubility of the catalyst, a solubilizer is frequently added to the solvent. This specific embodiment of a catalytic process is employed, for example, in the hydroformylation of olefins. According to EP-A2-0 353 770, the catalysts produced using the ionic phosphite ligands described have a high activity. The reaction of olefins with CO and $H_2$ leads preferentially to unbranched aldehydes and the low volatility of the ionic phosphites is advantageous when the reaction products are separated from the reaction mixture by distillation.

The known methods of carrying out catalytic reactions in ionic liquids are not yet satisfactory in every respect. Thus, the conversion of the starting materials and the selectivity in respect of the products are not always as efficient as demanded by industrial processes. The degree to which the catalyst metal, often a noble metal, is carried from the reaction mixture together with the reaction product is frequently not tolerable. When the reaction medium and final products are miscible, energy-intensive and, in the case of thermally labile products, technically complicated separation operations have to be carried out.

Catalysts based on metal complexes with ionic phosphites as ligands are used in conjunction with, as is shown by, for example, EP-A2-0 353 770, conventional reaction media, viz. organic solvents, and the use of the ionic phosphites is restricted by the limited solubility of these substances in organic media.

It is therefore an object of the invention to provide ionic liquids which have wide suitability as solvents for catalysts, may themselves be catalysts or components of catalyst systems and whose solvent capability for inorganic and organic substances, starting materials and reaction products can be matched to the respective requirements. They should preferably not mix with, at least, the reaction products so that there is the opportunity of separating starting materials and catalyst from the end products in a simple manner.

The object outlined above is achieved by nonaqueous ionic liquids of the formula $(Q^+)_a A^{a-}$, where $Q^+$ is a singly charged ammonium cation which may be substituted by organic radicals or the equivalent of a multiply charged ammonium cation which may be substituted by organic radicals, $A^{a-}$ is the anion of a sulfonated or carboxylated triester of phosphorous acid and a is an integer equal to or greater than 1.

It has surprisingly been found that the nonaqueous ionic solvents of the invention are very useful as reaction medium for reactions of, in particular, organic substances with organic or inorganic reactants. They are solvents for many catalysts used in chemical syntheses and can, owing to the presence of trivalent phosphorus, themselves act as catalysts or constituents of catalysts, e.g. of catalytically active metal complexes. Varying the structure of the ester anion and of the ammonium cation or mixing various compounds of the type provided by the invention with one another and/or with ester salts whose cation is not an ammonium ion makes it possible to prepare ionic solvents which are matched to individual requirements, e.g. in respect of their thermal behavior or their solvent capability for particular substances, either inorganic or organic.

The ammonium salts of sulfonated or carboxylated phosphorous triesters used according to the invention are formally derived from phosphorous acid by esterification with the ammonium salts of hydroxysulfonic acids or hydroxycarboxylic acids of the formula

$$(Qac)_b\text{-}Y\text{---}(OH)_c \qquad (1)$$

where ac is an acid radical, namely the sulfonic acid group $—SO_3^-$ or the carboxylic acid group $—COO^-$ and Q is, as already indicated above, a singly charged ammonium cation which may be substituted by organic radicals or the equivalent of a multiply charged ammonium cation which may be substituted by organic radicals.

Furthermore, Y in the formula (1) is an organic radical. Accordingly, the compounds represented by this formula are sulfonated or carboxylated hydroxy compounds derived from aliphatic, cycloaliphatic, aromatic and heterocyclic parent structures. The aliphatic compounds can be linear or branched and, like the cycloaliphatic compounds, saturated or unsaturated. The cycloaliphatic and aromatic compounds include both monocyclic and polycyclic structures. Likewise, the hydroxy acids of the phosphites used according to the invention include aliphatic-aromatic and also aromatic-aliphatic compounds. Possible heterocyclic compounds are saturated or unsaturated ring systems containing nitrogen, oxygen or sulfur as hetero atom. Two or more identical or different hetero atoms can also be present in the molecule. Furthermore, the heterocycle can also be substituted by alkyl radicals or aryl radicals or be fused with further ring systems, either aliphatic, aromatic or heterocyclic. All compounds may bear further substituents known to those skilled in the art which are chemically unreactive in their specific use as ionic liquid.

In particular, Y in the above formula (1) is a linear or branched, saturated aliphatic radical having a total of from 1 to 20 carbon atoms which may be substituted by hydroxy groups or by alkoxy radicals having from 1 to 10 carbon atoms. Y is preferably a saturated or unsaturated, monocyclic or polycyclic cycloaliphatic radical having from 5 to 14 carbon atoms in the ring or rings or a monocyclic or polycyclic aromatic radical having from 6 to 14 carbon atoms in the ring or rings. Both the cycloaliphatic radicals and the aromatic radicals may bear not only sulfonic acid or carboxylic acid radicals but also further substituents, namely alkyl radicals having from 1 to 20 carbon atoms, aryl, alkylaryl or aralkyl radicals having from 6 to 30 carbon atoms and cycloalkyl radicals having from 5 to 14 carbon atoms, also hydroxy groups and alkoxy radicals having from 1 to 10 carbon atoms. The aromatic radicals are preferably derived from benzene, from biphenyl, from naphthalene and from binaphthyl. A particularly useful arylalkyl radical has been found to be the readily available, substituted or unsubstituted benzyl radical. Alkylaryl radicals are preferably derived from toluene, ethylbenzene and the isomeric xylenes. Among the heterocycles, radicals of nitrogen-containing, saturated or unsaturated five- or six-membered rings, in particular pyridine, are of importance. Finally, b and c are each integers and are each at least 1; c is particularly preferably 1 or 2.

Sulfonated or carboxylated esters of phosphorous acid according to the invention include, in particular, compounds of the formula (2)

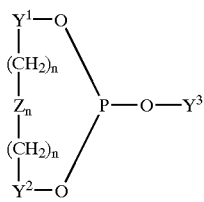

(2)

where $Y^1$, $Y^2$ and $Y^3$ are identical or different, are each an organic radical and are as defined for Y under formula (1). Z is a divalent bridging group and is $-CR^1R^2-$, where $R^1$ and $R^2$ are each, independently of one another, hydrogen or an alkyl radical having from 1 to 12 carbon atoms. Z may also be $-O-$, $-S-$, $-CO-$, $-CH_2-CO-CH_2-$; n are identical or different and are each 0 or 1, and when Z is $-CR^1R^2-$ are 1, 2 or 3. When n is 0, the radicals $Y^1$, $Y^2$ and $Y^3$ can be independent. However, two adjacent radicals $Y^1$ and $Y^2$, $Y^2$ and $Y^3$ or $Y^1$ and $Y^3$ can also be joined to one another and form, for example, a divalent radical. If $Y^1$ and $Y^2$ are each a radical derived from benzene, these two adjacent radicals may be, for example, linked by a single bond to form a divalent biphenyl radical. If adjacent radicals $Y^1$, $Y^2$, $Y^3$ are cycloaliphatic or aromatic structures, they can in the case of n=0 also be linearly fused. This then results, for example, in divalent, substituted or unsubstituted cycloaliphatic, aromatic or cycloaliphatic-aromatic radicals, e.g. divalent dicyclodecylene or tricyclotetradecylene radicals or divalent naphthylene or anthracylene radicals. Furthermore, the esters of the formula (2) contain at least one ac-radical, i e. at least one sulfonic acid group or one carboxyl group.

In the compounds of the formula (2), $Y^1$, $Y^2$, $Y^3$ are each preferably a radical derived from benzene, from naphthalene, from biphenyl or from binaphthyl which may in each case be substituted by one or more alkyl radicals having from 1 to 20 carbon atoms, by one or more aryl, aralkyl, alkylaryl radicals having from 6 to 30 carbon atoms and/or by one or more cycloalkyl radicals having from 5 to 14 carbon atoms, by hydroxy groups and/or alkoxy radicals having from 1 to 10 carbon atoms and/or by one or more acid radicals (-ac⁻). Z is, in particular, the radical $-CH_2-$, $-O-$, $-CO-$ or $-CH_2-O-CH_2-$.

The compounds corresponding to the formula (2) include sulfonates or carboxylates of trialkyl phosphites such as trimethyl phosphite, triethyl phosphite, butyl diethyl phosphite, tri-n-propyl phosphite, tri-n-butyl phosphite, tri-2-ethylhexyl phosphite, tri-n-octyl phosphite, tri-n-dodecyl phosphite, of dialkyl aryl phosphites such as dimethyl phenyl phosphite, diethyl phenyl phosphite, of alkyl diaryl phosphites such as methyl diphenyl phosphite, ethyl diphenyl phosphite and of triaryl phosphites such as triphenyl phosphite, phenyl biphenylene phosphite and trinaphthyl phosphite.

A further group of important sulfonated or carboxylated esters of phosphorous acid corresponding to the invention are polyphosphites of the formula (3)

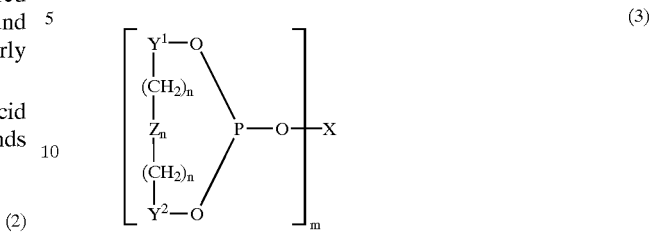

(3)

In this formula, $Y^1$ and $Y^2$ are identical or different and are as defined for Y under the formula (1) and for $Y^1$, $Y^2$ and $Y^3$ under the formula (2). The definitions of Z and n correspond to those given under the formula (2). X is an m-valent bridging group selected from among alkylene radicals, alkyleneoxyalkylene radicals, arylene radicals and aryl-$Z_n$-aryl radicals. m is an integer and is in the range from 2 to 6. Furthermore, the polyphosphite of the formula (3) contains at least one ac⁻ radical, i.e. at least one sulfonate ($-SO_3^-$) or carboxylate ($-COO^-$) group.

X is preferably an alkylene radical having from 2 to 18, in particular from 2 to 12, carbon atoms or an arylene radical having from 6 to 18 carbon atoms. When X is aryl-$Z_n$-aryl, Z is preferably $-CH_2-$, $-O-$, $-CO-$ or $-CH_2-CO-CH_2-$. The radicals X may likewise be substituted by one or more alkyl and/or alkoxy radicals and/or by one or more acid radicals (-ac⁻).

Further important representatives of the esters of phosphorous acid according to the invention have the formula (4) below.

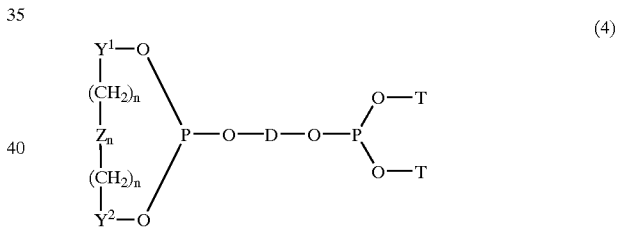

(4)

In this formula, $Y^1$ and $Y^2$ are identical or different and are as defined for Y under the formula (1) and for $Y^1$ and $Y^2$ under the formula (3). The definitions of Z and n correspond to those given under the formula (2) and the formula (3). D is a divalent hydrocarbon radical as bridging group, namely an alkylene radical having from 1 to 30 carbon atoms, an arylene, alkylarylene, arylalkylene radical having from 6 to 30 carbon atoms or an aryl-$Z_n$-aryl radical. T is a monovalent hydrocarbon radical having from 1 to 30 carbon atoms and may be an alkyl, aryl, aralkyl, alkylaryl or cycloalkyl radical. Furthermore, the phosphite of the formula (4) contains at least one ac⁻ radical, i.e. at least one sulfonate ($-SO_3^-$) or carboxylate ($-COO^-$) group.

The sulfonated or carboxylated esters of phosphorous acid can be obtained by transesterification (alcoholysis) of phosphorous esters with a salt, preferably the ammonium salt, of a hydroxysulfonic acid or a hydroxycarboxylic acid. For this purpose, the salt dissolved in an organic solvent is reacted with the phosphorous ester at from 20 to 200° C., preferably from 80 to 160° C. The reactants are usually used in equivalent amounts, even though it is also possible to use an excess of either reactant. The reaction is accelerated by catalysts such as amines, sodium, sodium alkoxides, aluminum trichloride, titanic esters or dialkyl phosphites. Phosphorous esters suitable for the transesterification are derived from aliphatic or aromatic hydroxy compounds, preferably ones containing from 1 to 12 carbon atoms. Examples of such phosphites are trimethyl phosphite, triethyl phosphite, butyl diethyl phosphite, tri-n-propyl phosphite, tri-n-butyl phosphite, tri-2-ethylhexyl phosphite, tri-n-octyl phosphite, tri-n-dodecyl phosphite, dimethyl phenyl phosphite, diethyl phenyl phosphite, triphenyl phosphite. A preferred organic phosphite is triphenyl phosphite.

Cations $Q^+$ present in the nonaqueous ionic liquids used according to the invention are, in particular, ammonium ions substituted by organic radicals, namely ammonium ions derived from monoamines or diamines. The ammonium ions of monoamines correspond to the formulae (5) and (6)

   (5)

and

   (6)

where $R^3$, $R^4$, $R^5$ and $R^6$ are identical or different and are each hydrogen, in particular with the proviso that at least one of $R^3$, $R^4$, $R^5$, $R^6$ is not hydrogen, or a linear or branched, aliphatic hydrocarbon radical having from 1 to 20 carbon atoms, a cycloaliphatic or aromatic hydrocarbon radical having from 6 to 20 carbon atoms or an alkoxy radical having from 1 to 10 carbon atoms. Examples of such radicals are alkyl, alkenyl, cycloalkyl, aryl, alkylaryl and aralkyl radicals.

Further cations which are useful in the nonaqueous ionic liquids used according to the invention are ions which are derived from saturated or unsaturated cyclic compounds or from aromatic compounds having a trivalent N atom in a 4- to 10-membered, preferably 5- or 6-membered, heterocyclic ring. Such cations can be represented in simplified form (i.e. without indication of the precise position and number of double bonds in the molecule) by the formulae (7) and (8) below.

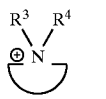   (7)

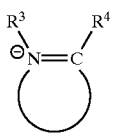   (8)

$R^3$ and $R^4$ in these formulae are as defined above. Examples of cyclic amines of the abovementioned type are pyrrolidine, dihydropyrrole, pyrrole, indole, carbazole, piperidine, pyridine, the isomeric picolines and lutidines, quinoline and i-quinoline.

Preferred cations are derived from aliphatic, cycloaliphatic or aromatic diamines. They have the formulae (9) and (10)

   (9)

   (10)

where $R^3$, $R^4$, $R^5$, $R^6$, $R^7$ and $R^8$ are identical or different and are each hydrogen, a linear or branched aliphatic hydrocarbon radical having from 1 to 20 carbon atoms, a cycloaliphatic or aromatic hydrocarbon radical having from 6 to 30 carbon atoms, an alkylaryl radical having from 7 to 40 carbon atoms or an alkoxy radical having from 1 to 10 carbon atoms. G is an alkylene radical $(\text{---CHR}^9\text{---})_d$, where $R^9$ is hydrogen or a hydrocarbon radical having from 1 to 5 carbon atoms and d is an integer from 1 to 8, preferably from 2 to 6, an arylene radical having from 6 to 30 carbon atoms or an alkylenearyl radical having from 7 to 40 carbon atoms. Examples of hydrocarbon radicals $R^3$, $R^4$, $R^5$, $R^6$, $R^7$ and $R^8$ are alkyl, alkenyl, cycloalkyl, aryl, alkylaryl or arylalkyl radicals, e.g. methyl, ethyl, propyl, i-propyl, butyl, sec-butyl, t-butyl, amyl, methylene, ethylidene, phenyl, benzyl. $R^9$ is, for example, a methyl, ethyl, n-propyl or i-propyl radical or one of the isomeric butyl radicals. Examples of G are the radicals methylene, ethylene, propylene, butylene, 1,4-phenylene, 1,4-tolylene, 1,4-xylylene, 1,1'-biphenyl-4,4'-diyl, 1,4-naphthylene, 1,1'-binaphthyl-2,2'-diyl.

Cations which are particularly useful for the nonaqueous ionic liquids used according to the invention are derived from 1-amino-3-dialkylamino-propanes of the formula (11)

   (11)

as diamines, where $R^{10}$ and $R^{11}$ are identical or different linear or branched alkyl radicals having from 4 to 20 carbon atoms, for example n-butyl, n-pentyl, n-hexyl, n-heptyl, i-heptyl, n-octyl, i-octyl, n-nonyl, i-nonyl, n-decyl, i-decyl, n-undecyl, i-undecyl, n-dodecyl or i-dodecyl.

Further advantageous cations for the nonaqueous ionic liquids used according to the invention are derived from the following amines: 1-amino-3-(di-n-heptyl)aminopropane, 1-amino-3-(di-i-heptyl)aminopropane, 1-amino-3-(di-n-octyl)aminopropane, 1-amino-3-(di-i-octyl)aminopropane, 1-amino-3-(di-n-nonyl)aminopropane, 1-amino-3-(di-i-nonyl)aminopropane, 1-amino-3-(di-n-undecyl)aminopropane, 1-amino-3-(di-i-undecyl)aminopropane, 1-amino-3-(di-n-dodecyl)aminopropane or 1-amino-3-(di-i-dodecyl)aminopropane.

The above-described 1-amino-3-dialkylaminopropanes are readily obtainable from N,N-(dialkyl)amines and acrylonitrile (cf. Ullmanns Encyclopedia of Industrial Chemistry, Vol. A2, 1985).

Finally, the diamines which give cations suitable for the nonaqueous ionic liquids used according to the invention also include heterocyclic compounds. These include saturated or unsaturated and also aromatic compounds having two trivalent N atoms in a 4- to 10-membered, preferably 5- or 6-membered, heterocyclic ring. These compounds may be substituted both on the carbon atoms and on the nitrogen atoms, preferably by alkyl radicals having from 1 to 10 carbon atoms and by phenyl radicals. They can also be fused with substituted or unsubstituted benzene rings and/or cyclohexane rings to form polycyclic structures. Examples of such compounds are pyrazole, 3,5-dimethylpyrazole, imidazole, benzimidazole, dihydropyrazole, pyrazolidine, pyridazine, pyrimidine, pyrazine, 2,3-, 2,5- and 2,6-dimethylpyrazine, cimoline, phthalazine, quinazoline, phenazine and piperazine. Cations of the formula (12)

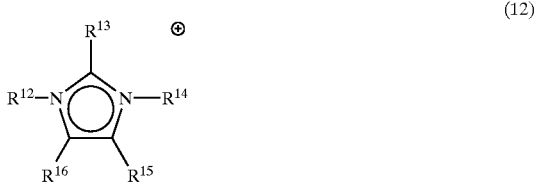   (12)

derived from imidazole and its alkyl and phenyl derivatives have been found to be particularly useful as constituents of the novel ionic liquids. In this formula, $R^{12}$, $R^{13}$, $R^{14}$, $R^{15}$ and $R^{16}$ are identical or different. They are each hydrogen, a $C_1$–$C_{30}$-alkyl radical, a $C_6$–$C_{40}$-aryl radical, a $C_7$–$C_{40}$-alkylaryl radical or an $SiR_3^{17}$ radical in which $R^{17}$ is a $C_1$–$C_{30}$-alkyl radical or a $C_6$–$C_{40}$-aryl radical. Examples of such cations are: 1-ethyl-3-methyl-2,4,5-H-imidazolium, 1-propyl-3-methyl-2,4,5-H-imidazolium, 1-butyl-3-methyl-2,4,5-H-imidazolium, 1,3,4,5-tetramethyl-2-H-imidazolium, 2,4,5-trimethyl-1,3-H-imidazolium, 1,2,3,4,5-pentamethylimidazolium, 1,2,3,5-tetramethyl-4-H-imidazolium, 1,2,3,4-tetramethyl-5-H-imidazolium, 1,3,4,5-tetraphenyl-2-H-imidazolium, 1,3-dimethyl-4,5-diphenyl-2-H-imidazolium, 1-ethyl-3-isopropyl-2,4,5-H-imidazolium, 1-butyl-3-octanyl-2,4,5-H-imidazolium, 1-propyl-3-octanyl-2,4,5-H-imidazolium, 1-ethyl-3-octanyl-2,4,5-H-imidazolium, 1-methyl-3-octanyl-2,4,5-H-imidazolium, 1,3-diisopropyl-4,5-dimethyl-2-H-imidazolium, 1,4,5-trimethyl-3-trimethylsilyl-2-H-imidazolium, 2-ethyl-4-methyl-1,3,5-H-imidazolium, 1,3-adamantyl-4,5-dimethyl-1-H-imidazolium, 1,2,4,5-tetramethyl-3-H-imidazolium, 1-methyl-2,3,4,5-H-imidazolium, 1,3-dimethyl-2,4,5-H-imidazolium, 2-methyl-4,5-ethyl-1,3-H-imidazolium, 2,4,5-trimethyl-1,3-H-imidazolium, 1-ethyl-2,3,4,5-H-imidazolium, 1,3-diethyl-4,5-dimethyl-2-H-imidazolium, 1,3-diphenyl-4,5-dimethyl-2-H-imidazolium, 1,3-diphenyl-2,4,5-H-imidazolium, 1,3-dimethoxy-4,5-dimethyl-2-H-imidazolium, 1-trimethylsilyl-2,3,5-trimethyl-4-H-imidazolium.

Furthermore, ionic liquids which are based on sulfonated or carboxylated triesters of phosphorous acid and whose cations are derived from polyamines have been found to be very useful. Examples of such polyamines are hexamethylenetetramine and purine and also their derivatives.

The preparation of the nonaqueous ionic liquids used according to the invention starts out from salts of the above-described sulfonated or carboxylated esters of phosphorous acid. Suitable salts are alkali metal and alkaline earth metal salts, preferably sodium or potassium salts. They are used as aqueous solutions of the pure compounds or else as mixtures of various salts.

To obtain the nonaqueous ionic liquids used according to the invention, the amine is protonated or alkylated by means of acids and/or alkylating agents in the presence of an aqueous solution of salts of the sulfonated or carboxylated phosphorous esters to form the singly or multiply charged cation.

As acids, it is possible to use hydrogen acids, e.g. tetrafluoroboric acid or hexafluorophosphoric acid, or oxygen acids, e.g. phosphoric acid, sulfuric acid, nitric acid, also phosphonic acids having from 1 to 20 carbon atoms or sulfonic acids having from 1 to 20 carbon atoms. Preference is given to using aqueous sulfuric acid or phosphoric acid solutions which generally contain from 10 to 30% by weight of acid.

Alkylating agents which can be used are, for example, monoalkyl sulfates or dialkyl sulfates or dialkyl carbonates having from 1 to 41 carbon atoms or alkyl halides having from 1 to 10 carbon atoms.

Acid and/or alkylating agent are/is usually added in an amount of from 0.9 to 2.0, preferably from 1.0 to 1.5, equivalents per equivalent of the amines used. When using an acid, the pH after addition of the acid is from 2 to 5, preferably from 3 to 4.

To replace the metal ions in the salts of the phosphorous esters by ammonium ions, the amines are advantageously used in an excess above the stoichiometrically required amount, based on the metal ions. This excess is generally up to 5 equivalents, preferably up to 1 equivalent.

The amine is usually used as a 20–70% strength by weight, preferably 40–60% strength by weight, solution in an organic solvent. Suitable organic solvents are aliphatic or aromatic hydrocarbons such as benzene, toluene, o-xylene, m-xylene, p-xylene, mesitylene, n-heptane, n-octane, cyclohexane or else ethers such as 1,4-dioxane or tetrahydrofuran. Preference is given to using toluene or cyclohexane.

The addition of the acid and/or the alkylating agent to the mixture of the aqueous solution of the salt or salts of the phosphorous ester and the organic solution of the amine is carried out at from 0 to 60° C., preferably from 20 to 30° C. The duration of the addition is generally from 0.5 to 3 hours, preferably from 1 to 2 hours.

The reaction results in three phases: a lower aqueous phase in which the alkali metal and/or alkaline earth metal salts liberated from the esters of phosphorous acid are dissolved, a middle phase, namely the nonaqueous ionic liquid, and an upper phase comprising the organic solvent in which excess amine may be present. The desired nonaqueous ionic liquid can be obtained by simple phase separation.

To ensure satisfactory formation of the three phases, it may be advantageous to add further organic solvent to the mixture after addition of the acid and/or the alkylating agent. Preference is given to using the same organic solvent as that used for dissolving the amine. The amount of organic solvent which has to be added to achieve separation into three phases can be determined by simple preliminary tests.

In a further embodiment of the preparative method, an aqueous solution of salts of the phosphorous esters is firstly treated with an acid and/or an alkylating agent, after which the amine dissolved in an organic solvent is added. It is also possible to react the amine to be protonated and/or to be alkylated with the acid and/or the alkylating agent first and subsequently to add an aqueous solution of the salts of the sulfonated or carboxylated esters of phosphorous acid.

Finally, it is also possible to convert the salts of the sulfonated or carboxylated phosphorous esters into the free sulfonic acid or carboxylic acid by treatment with a cation exchanger in the $H^+$ form and then to neutralize this acid with the amine.

The nonaqueous ionic liquids of the invention are, like other ionic liquids, very useful as inert, thermally stable reaction media. Varying the chemical structure of the ionic phosphorous esters both in the cationic part and in the anionic part of the molecule or mixing various esters or salts makes it possible to develop liquids which are tailored to specific requirements. In this way, media in which the starting materials and reaction products and, if a catalytic reaction is to be carried out, the catalysts, too, are soluble can be produced. If desired, the solubility of one or more reactants or of the reaction product or products can be improved by addition of known solubilizers to the ionic liquid. The reaction then occurs in a homogeneous phase. A variant of the homogeneous reaction can involve a reaction product which is not soluble in the reaction medium, precipitates from the reaction mixture and can therefore be separated from the reaction mixture in a simple manner. Finally, appropriate selection of the molecular constituents of the ionic liquid according to the invention or mixtures thereof also makes it possible to provide reaction media which, in the case of catalytic reactions, act as solvents only for the catalyst, so that the reactants react with one another at the phase interface to the catalyst solution and the reaction product forms a separate phase. This reaction variant makes it possible to reuse the catalyst without problems and, in addition, simplifies its regeneration and work-up.

When the ionic liquids are used as solvents for catalysts, a particularly important aspect is that the novel ionic liquids act as ligands toward transition metals and can form catalytically active complexes with them because of the presence of trivalent phosphorus in the molecule of the ionic liquid, so that they can themselves act as component of a catalyst system. When they perform this function, which can be described as "ligand liquid", they allow high molar ratios of ligand to transition metal of 100 and more. Such high ligand excesses are frequently desired since they stabilize the catalytically active metal complexes and in this way lead to a considerable increase in the catalyst life and to maintenance of a constant catalyst selectivity over a long period of time.

The novel ionic liquids can be used as solvents and catalyst components for catalysts based on transition metals of groups VI, VII and VIII of the Periodic Table of the Elements. Particularly useful catalyst metals are cobalt, rhodium, iridium, ruthenium, palladium or platinum. To produce the catalysts, the transition metals are used in elemental form as metal or as compounds. In metallic form, they are either used as finely divided particles or are deposited in a thin layer on a support such as activated carbon, calcium carbonate, aluminum silicate or alumina. Compounds employed are, for example, metal oxides or salts of inorganic hydrogen acids and oxygen acids, e.g. chlorides, nitrates, sulfates or phosphates, also carbonyl compounds, complexes such as cyclooctadienyl complexes, cyclopentadienyl complexes, acetylacetonato complexes or salts of aliphatic monocarboxylic and polycarboxylic acids, e.g. acetates, propionates, butyrates, valerates, 2-ethylhexanoates, oxalates or malonates. Preference is given to using the 2-ethylhexanoates.

The catalyst systems suitable for the respective purpose can firstly be formed in a preformation step and then be added to the reaction mixture. In this case, the desired amount of the transition metal, either in metallic form or as a compound, is added to the nonaqueous ionic ligand liquid. The reactants are then introduced and reacted in the presence of the catalyst.

The catalyst system can be produced equally successfully under reaction conditions, i.e. in the presence of the starting materials to be reacted.

The reactions can be carried out either batchwise or continuously. After the reaction is complete, the desired products and the catalyst system are present in separate phases which can be separated from one another by simple phase separation. After phase separation has been carried out, the catalyst system can be returned to the reaction process.

The use of the nonaqueous ionic ligand liquids of the invention in chemical processes catalyzed by transition metals makes it possible to dispense with the addition of further anions which do not serve as ligands.

The following example illustrates the invention without restricting its scope. The phosphite used in the example was prepared by a method analogous to that reported in the literature (EP 353 770).

EXAMPLE

In a 1 l three-necked flask provided with a bottom outlet, a solution of 65.3 g of 1-amino-3-(di-i-nonylamino)propane (200 mmol) in 400 ml of toluene was slowly added at room temperature to 103.9 g of the sodium salt of 4-sulfophenyl-3,3'-di-t-butyl-5,5'-dimethoxy-1,1'-biphenyl-2,2'-diyl phosphite (200 mmol) dissolved in 396 g of distilled water. While stirring, 98 g of sulfuric acid (20% strength by weight) are added dropwise over a period of 2 hours. After switching off the stirrer, 3 phases are formed, and these were separated and analyzed for P(III). All the P(III) is present in the 280 g of the middle phase, which forms the nonaqueous, ionic ligand liquid. The lower phase comprises sodium hydrogen sulfate or sodium sulfate, while the upper phase comprises mainly toluene.

What is claimed is:

1. A nonaqueous ionic liquid of the formula $(Q^+)_a A^{a-}$, wherein $Q^+$ is a singly charged ammonium cation which may be substituted by organic radicals or the equivalent of a multiply charged ammonium cation which may be substituted by organic radicals, $A^{a-}$ is the anion of a sulfonated or carboxylated triester of phosphorous acid and a is an integer equal to or greater than 1 wherein the alcohol component of the phosphorous triester corresponds to the formula $$(Qac)_b\text{—}Y\text{—}(OH)_c \quad (I)$$

where Y is selected from the group consisting of A, X, Y' and Z, Q is an ammonium cation which may be substituted by organic radicals or the equivalent of a multiply charged ammonium cation which may be substituted by organic radicals, ac is a sulfonic acid or carboxylic acid radical and b and c are integers which are each equal to or greater than 1, A is a linear or branched, saturated aliphatic of 1 to 20 carbon atoms which may be substituted by hydroxy groups or alkoxy of 1 to 10 carbon atoms, X is a saturated or unsaturated. monocyclic or polycyclic cycloaliphatic of 5 to 14 carbon atoms in the ring or rings and may be substituted by a member selected from the group consisting of alkyl of 1 to 20 carbon atoms, aryl, alkaryl and aralkyl of 6 to 30 carbon atoms, cycloalkyl of 5 to 14 carbon atoms, hydroxy, and alkoxy of 1 to 10 carbon atoms, Y' is a monocyclic or polycyclic aromatic of 6 to 14 carbon atoms in the ring or rings and may be substituted by a member selected from the group consisting of alkyl of 1 to 20 carbon atoms, aryl, alkylaryl and aralkyl of 6 to 30 carbon atoms, cycloalkyl of 5 to 14 carbon atoms, hydroxy and alkoxy of 1 to 10 carbon atoms and Z is a saturated or unsaturated heterocyclic which contains a hetero atom or a plurality of hetero atoms individually selected from the group consisting of N, O, S in the molecule and may be substituted by alkyl or aryl or be fused with aliphatic, cycloaliphatic or aromatic ring systems.

2. A nonaqueous ionic liquid as claimed in claim 1, wherein the alcohol component of the phosphorous triester corresponds to the formula $$(Qac)_b\text{—}Y\text{—}(OH)_c \quad (I)$$

where Y is selected from the group consisting of A, X, Y' and Z, Q is an ammonium cation which may be substituted by organic radicals or the equivalent of a multiply charged ammonium cation which may be substituted by organic radicals, ac is a sulfonic acid or carboxylic acid radical and b and c are integers which are each equal to or greater than 1.

3. A nonaqueous ionic liquid as claimed in claim 2, wherein Y is a linear or branched, saturated aliphatic of 1 to 20 carbon atoms which may be substituted by hydroxy groups or alkoxy of 1 to 10 carbon atoms.

4. A nonaqueous ionic liquid as claimed in claim 2, wherein Y is a saturated or unsaturated, monocyclic or polycyclic cycloaliphatic of 5 to 14 carbon atoms in the ring or rings and may be substituted by a member selected from the group consisting of alkyl of 1 to 20 carbon atoms, aryl, alkaryl and aralkyl of 6 to 30 carbon atoms, cycloalkyl of 5 to 14 carbon atoms, hydroxy an alkoxy of 1 to 10 carbon atoms.

5. A nonaqueous ionic liquid as claimed in claim 2, wherein Y is a monocyclic or polycyclic aromatic of 6 to 14 carbon atoms in the ring or rings and may be substituted by a member selected from the group consisting of alkyl of 1 to 20 carbon atoms, aryl, alkylaryl and aralkyl of 6 to 30 carbon atoms, cycloalkyl of 5 to 14 carbon atoms, hydroxy and alkoxy of 1 to 10 carbon atoms.

6. A nonaqueous ionic liquid as claimed in claim 5, wherein the aromatic radical is selected from the group consisting of benzene, toluene, ethylbenzene, isomeric xylenes, biphenyl, naphthalene and binaphthyl and the aralkyl is a substituted or unsubstituted benzyl.

7. A nonaqueous ionic liquid as claimed in claim 2, wherein Y is a saturated or unsaturated heterocyclic which contains a hetero atom or a plurality of hetero atoms individually selected from the group consisting of N, O, S in the molecule and may be substituted by alkyl or aryl or be fused with aliphatic, cycloaliphatic or aromatic ring systems.

8. A nonaqueous ionic liquid as claimed in claim 7, wherein the heterocyclic is derived from a nitrogen-containing saturated or unsaturated five-membered or six-membered cyclic compound.

9. A nonaqueous ionic liquid as claimed in claim 1 comprising ammonium ions derived from monoamines of the formula (5) or (6)

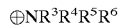 (5)

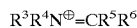 (6)

wherein at least one of $R^3$, $R^4$, $R^5$, $R^6$ is not hydrogen, or aliphatic hydrocarbon of 1 to 20 carbon toms, a cycloaliphatic or aromatic hydrocarbon of 6 to 20 carbon atoms or alkoxy of 1 to 10 carbon atoms.

10. A nonaqueous ionic liquid as claimed in claim 1 comprising ammonium ions of the formula

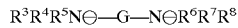 (9)

or

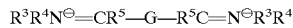 (10)

wherein $R^3$, $R^4$, $R^5$, $R^6$, $R^7$ and $R^8$ are individually selected from the group consisting of hydrogen, hydrocarbon of from 1 to 20 carbon atoms, cycloaliphatic or aromatic hydrocarbon of 6 to 30 carbon atoms, alkylaryl of 7 to 40 carbon atoms and alkoxy of 1 to 10 carbon atoms, G is $(-CHR^9-)_d$, wherein $R^9$ hydrogen or hydrocarbon of 1 to 5 carbon atoms and d is an integer from 1 to 8, arylene of 6 to 30 carbon atoms or alkylenearyl of 7 to 40 carbon atoms.

11. A process for preparing nonaqueous ionic liquids as claimed in claim 1, which comprises converting an aqueous solution of salts of sulfonated or carboxylated phosphorous esters into the free sulfonic acid or carboxylic acid by treatment with a cation exchanger in the $H^+$ form and then neutralizing this acid with the amine.

12. A process for preparing nonaqueous ionic liquids as claimed in claim 1, which comprises reacting a solution of the amine forming the cation with an acid and/or an alkylating agent in the presence of an aqueous solution of alkali metal and/or alkaline earth metal salts of the sulfonated or carboxylated phosphorous esters.

13. The process for preparing nonaqueous ionic liquids as claimed in claim 12, wherein from 0.9 to 2.0, in particular from 1.0 to 1.5, equivalents of acid and/or alkylating agent are used per equivalent of amine.

14. The process for preparing nonaqueous ionic liquids as claimed in claim 12, wherein phosphoric acid, sulfuric acid, nitric acid, a phosphoric acid having from 1 to 20 carbon atoms or a sulfonic acid having from 1 to 20 carbon atoms is used as acid.

15. The process for preparing nonaqueous ionic liquids as claimed in claim 12, wherein an aqueous solution of phosphoric acid of sulfuric acid is used as acid.

16. The process for preparing nonaqueous ionic liquids as claimed in claim 12, wherein a monoalkyl or dialkyl sulfate or a dialkyl carbonate having from 1 to 41 carbon atoms or an alkyl halide having from 1 to 10 carbon atoms is used as alkylating agent.

17. The process for preparing nonaqueous ionic liquids as claimed in claim 12, wherein the amine is used as a solution in benzene, toluene, o-xylene, n-xylene, p-xylene, mesitylene, n-heptane, n-octane, cyclohexane, tetrahydrofuran or 1 m4-dioxane.

18. The process for preparing nonaqueous ionic liquids as claimed in claim 12, wherein the reaction between acids and/or alkylating agent, salt of the phosphorous ester and amine is carried out at from 0 to 60° C.

19. A non-aqueous ionic liquid of claim 8 wherein the heterocyclic is pyridine.

* * * * *